United States Patent [19]

Horikoshi et al.

[11] Patent Number: 4,476,023
[45] Date of Patent: Oct. 9, 1984

[54] GRANULOCYTE-SEPARATING MATERIAL AND GRANULOCYTE SEPARATOR

[75] Inventors: Katsunori Horikoshi; Tsutomu Abe, both of Fuji, Japan

[73] Assignee: Asahi Kasei Kogyo Kabushiki Kaisha, Osaka, Japan

[21] Appl. No.: 425,039

[22] Filed: Sep. 27, 1982

Related U.S. Application Data

[62] Division of Ser. No. 239,259, Mar. 2, 1981, Pat. No. 4,370,381.

[30] Foreign Application Priority Data

Mar. 12, 1980 [JP] Japan ................................ 55-30247
Mar. 12, 1980 [JP] Japan ................................ 55-30248

[51] Int. Cl.³ .............................................. B01D 15/04
[52] U.S. Cl. ..................................... 210/446; 428/392; 428/36; 210/282; 210/927
[58] Field of Search ................. 428/392; 210/282, 927; 604/4-6

[56] References Cited

U.S. PATENT DOCUMENTS

| | | | |
|---|---|---|---|
| 3,448,041 | 6/1969 | Swank | 210/927 X |
| 3,462,361 | 8/1969 | Greenwalt et al. | 210/927 X |
| 3,630,683 | 12/1971 | Robb | 210/282 X |
| 3,647,624 | 3/1972 | Evenson | 604/5 X |
| 4,050,451 | 9/1977 | Columbus | 210/927 X |
| 4,202,775 | 5/1980 | Abe et al. | 210/927 X |
| 4,246,107 | 1/1981 | Takenaka et al. | 210/927 X |

*Primary Examiner*—George F. Lesmes
*Assistant Examiner*—Nancy A. B. Swisher
*Attorney, Agent, or Firm*—Sprung, Horn, Kramer & Woods

[57] ABSTRACT

Granulocytes are advantageously collected from blood cell suspensions, especially blood or other body fluids, by bringing the blood cell suspensions into contact with a granulocyte-separating material comprising a carrier, such as a fiber, having supported thereon a fatty acid derivative containing a fatty acid moiety having 10 to 22 carbon atoms, whereby granulocytes are adsorbed on the granulocyte-separating material; and then, recovering the adsorbed granulocytes therefrom.

1 Claim, 2 Drawing Figures

GRANULOCYTE-SEPARATING MATERIAL AND GRANULOCYTE SEPARATOR

This is a division of application Ser. No. 239,259, filed Mar. 2, 1981, now U.S. Pat. No. 4,370,381.

BACKGROUND OF THE INVENTION

1. Field of the Invention

The present invention relates to a granulocyte-separating material for collecting very simply granulocytes with a high purity in high yields from blood cell suspensions, such as blood and other body fluids. The present invention also relates to a granulocyte collector comprising this granulocyte-separating material.

2. Description of the Prior Art

Recently, not only whole blood transfusion, but also component transfusion has been performed in which a component, for example, an erythrocyte, leukocyte, platelet or plasma component, is transfused. Especially, transfusion of granulocytes has been applied widely to remedy infectious diseases in patients who suffer from a granulocytopenia, leukemia or aplastic anemia or for recovery of a reduction in the number of granulocytes due to the administration of carcinostatic agents or radiation. Since the life of granulocytes is short, granulocytes to be used for transfusion should be collected promptly from healthy doners by an ectosomatic circulation method.

Methods for collection of granulocytes are roughly divided into two types, that is, the continuous centrifugal separation method and the adsorption-desorption method using fibers.

The continuous centrifugal separation method is advantageous in that damage of hemocytes can be reduced. However, this method is defective in that the apparatus used is complicated and expensive, large quantities of lymphocytes are included in a collected granulocyte suspension and the yield of granulocytes is low.

The adsorption-desorption method using fibers is advantageous in that the intended collection can be attained by the use of a cheap apparatus having a simple structure and incorporation of lymphocytes in the collected product can be reduced to a low level. However, when fibers are used in this adsorption-desorption method, as in current cases, the operation of tapping a vessel packed with fibers while passing a recovery liquid therethrough is indispensable for recovery of granulocytes adhering to the fibers and, in consequence, the recovered granulocytes become poor in such functions as the bactericidal activity and chemotactic activity and morphological changes, such as formation of voids, are caused. Furthermore, this method is disadvantageous in that a medical operator is compelled to perform the tapping operation for about 10 minutes.

SUMMARY OF THE INVENTION

We researched the behavior of the adhesion (or adsorption) of granulocytes to the surfaces of solids with a view to eliminating the foregoing defects of the conventional methods. It was found that when a derivative of fatty acid having 10 to 22 carbon atoms is deposited or adsorbed on the surface of a solid, the adhesion of granulocytes is reduced and granulocytes can easily be recovered therefrom and undesirable deformation collected granulocytes is remarkably controlled while reduction of the functions of the granulocytes is prevented. We have now completed the present invention based on this finding.

In accordance with one fundamental aspect of the present invention, there is provided a granulocyte-separating material comprising a carrier having supported thereon a fatty acid derivative containing a fatty acid moiety having 10 to 22 carbon atoms. Furthermore, in accordance with other aspects of the present invention, there are provided a granulocyte collector comprising the above-mentioned granulocyte-separating material packed in a vessel having a blood cell suspension introduction inlet and a blood cell suspension discharge outlet and a method for collecting granulocytes by using this granulocyte separator.

DESCRIPTION OF THE PREFERRED EMBODIMENTS

Figure 1:
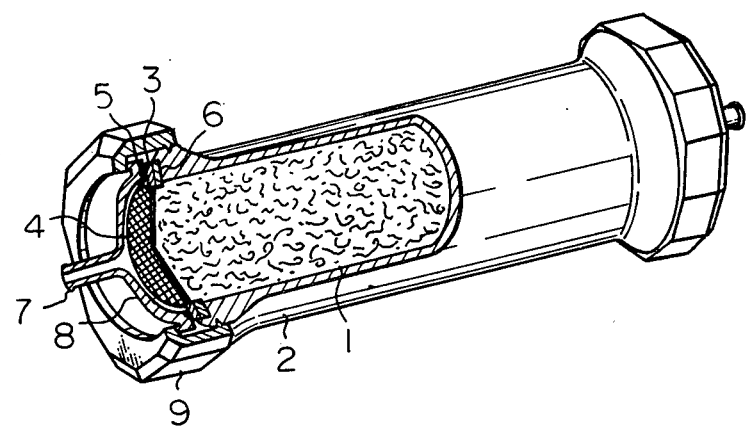
FIG. 1 is a partially sectional perspective view of one form of the granulocyte collector according to the present invention; and, FIG. 2 is a longitudinal sectional view of the granulocyte collector shown in FIG. 1.

The granulocyte-separating material according to the present invention may be prepared, for example, by the following procedures.

In 100 ml of an organic solvent are dissolved 0.1 to 10 g of a fatty acid derivative, and 1 to 10 g of a carrier insoluble in the organic solvent and water, such as a fiber, is dipped in the solution. This dipping treatment is conducted for 1 to 60 minutes. Then, the organic solvent is completely removed by drying. Thus, there is obtained a granulocyte-separating material in which the fatty acid derivative is deposited or adsorbed on the carrier in an amount of 0.1 to 100 mg per gram of the carrier.

As the derivative of the fatty acid having 10 to 22 carbon atoms, there are used alcohol esters and amides of fatty acids having 10 to 22 carbon atoms. For example, there can be mentioned esters of the fatty acids with alcohols such as methanol, ethanol, propanol and long-chain alcohols, glycol, glycerin, polyethylene glycol, monosaccharides and polysaccharides; and amides of the fatty acids with α-, β- and γ-amino acids, sphingosine and amidosaccharides. There are also used phospholipids such as derivatives of glycerophosphoric acid and sphingosinephosphoric acid. As the phospholipid, there can be mentioned, for example, phosphatidic acid, phosphatidyl choline (lecithin), phosphatidyl serine, phosphatidyl inositol and sphingomyelin. The origin of lecithin is not particularly critical, but lecithin derived from egg yolk is especially preferred.

It is preferable that the fatty acid constituting the above-mentioned fatty acid be unsaturated, because the unsaturated fatty acid derivative is deposited or adsorbed on the surface of the carrier in a good condition. For example, myristoleic acid, palmitoleic acid, oleic acid, linoleic acid and linolenic acid are preferably used. Unsaturated fatty acids having 18 carbon atoms, such as oleic acid, linoleic acid and linolenic acid, are especially preferred.

In order to obtain a good adhesion of the fatty acid derivative to the surface of the carrier, it is preferred that the phase transition temperature of the fatty acid derivative from a solid to a liquid or liquid crystal be not higher than 45° C.

Any of the organic solvents capable of dissolving the fatty acid derivative therein, but not dissolving or modifying the carrier, can be used as the liquid medium in which the fatty acid derivative is dissolved. For example, there can be used ethanol, diethyl ether, chloroform, carbon tetrachloride, ethylene dichloride and acetone.

The carrier used may be in any form of a film, a granule, a powder or a fiber. A carrier in the form of a pad of fibers is especially preferred because of ease in handling.

As the material used for the carrier, there can be mentioned, for example, nylon, polyester, polypropylene, polyacrylonitrile, cotton, rayon and cuprammonium rayon.

The phenomenon on which the present invention is based has not completely been elucidated. However, it is believed that the effect of the present invention will be attained according to the following mechanism. The granulocyte-separating material of the present invention comprising a fatty acid derivative deposited on a carrier hardly adsorbs thereon plasma proteins such as fibrinogen. Since such plasma proteins participate in the strong adhesion of granulocytes, it is considered that, by the above characteristic of the granulocyte-separating material of the present invention, the adhesion of granulocytes to the surface of the separating material is controlled or mitigated and thus the collected granulocytes can be recovered without substantial reduction of the functions of the granulocytes.

The effect of the surface treatment with the fatty acid derivative is prominent also when granulocytes adsorbed on the separating material are recovered therefrom by mechanical means.

In the method in which granulocytes adsorbed on the separating material are separated and recovered by means of tapping, as is popularly employed in customary procedures, the recovery ratio varies depending upon the degree of tapping, and at least 90% of the adsorbed granulocytes can be recovered when the separating material is tapped most strongly. However, in order to recover granulocytes in a manner in which the morphological change or reduction of the functions is minimized, it is advantageous that the tapping operation is carried out to such a degree that about 70% of the adsorbed granulocytes can be recovered.

Recovery of granulocytes is possible also by utilizing a pulsating current of a recovery liquid giving a weaker stimulus than the tapping operation. According to this customary method, however, only about 20 to about 30% of the granulocytes adsorbed on the separating material can ordinarily be recovered. This phenomenon suggests that among the granulocytes adsorbed on the separating material, only those adsorbed most weakly and suffering from the lowest reduction of the functions can be recovered according to this customary method.

In contrast to the above-mentioned customary method using a pulsating pump, granulocytes adsorbed on the separating material according to the present invention can easily be recovered therefrom, and under mild conditions using a pulsating pump, the granulocyte recovery ratio can be increased by more than 20%. That is, when the granulocyte-separating material of the present invention is used, granulocytes adsorbed thereon can be advantageously recovered therefrom not only according to the tapping method but also according to the pulsating current method. It is believed that adoption of the pulsating current method instead of the tapping method will result in mitigation of the labor of a medical operator.

When granulocytes are separated by using the separating material of the present invention, it is preferred that a citric acid salt capable of chelating a calcium ion taking an important role in the adhesion of granulocytes and a serum protein effective for maintaining the functions of granulocytes be incorporated into a fluid to be treated. When granulocytes are collected from a healthy donor according to an ectosomatic circulation method, it is preferred that an AB type serum be used as the serum protein.

The granulocyte collector of the present invention comprises a vessel having a blood cell suspension introduction inlet and a blood cell suspension discharge outlet and the above-mentioned granulocyte-separating material packed in said vessel, in which an introduced blood cell suspension passes through the vessel while having contact with the packed granulocyte-separating material.

When the carrier is comprised of a fiber, it is preferred that the packing density of the granulocyte-separating material be 0.05 to 0.20 $g/cm^3$. When the packing density is less than 0.05 $g/cm^3$, spaces among fibers are too large and the yield of granulocytes is reduced to an unacceptable extent. When the packing density exceeds 0.20 $g/cm^3$, spaces among fibers are too small and non-specific adhesion of blood components is caused, resulting in drastic reduction of the yield. It is preferred that the diameter of the fiber used be in the range of from 10 to 50 microns. If the fiber diameter is smaller than 10 microns, non-specific adsorption of lymphocytes and platelets, in addition to granulocytes, is liable to occur. If the fiber diameter exceeds 50 microns, the total surface area is diminished and the yield of granulocytes is reduced.

A preferred embodiment of the granulocyte collector of the present invention will now be described in detail with reference FIGS. 1 and 2.

A granulocyte-separating material 1 is packed in a cylinder 2. A mesh net 4 having the periphery welded and fixed through a peripheral ring 3 is disposed at the opening on each end of the cylinder 2. The mesh net 4 is secured to each opening of the cylinder 2 by clamping silicone packings 5 and 6 mounted to sandwich the mesh net 4 therebetween. A lid 8, having a blood cell suspension inlet or outlet 7 formed at the center thereof, is capped on the mesh net 4 at each end of the cylinder 2. Each lid 8 is clamped and secured together with the mesh net 4 by a clamping ring 9 screwed to the periphery of each end of the cylinder 2.

The granulocyte-separarting material 1 is held in the cylinder 2 between a pair of mesh nets 4. The blood cell suspension inlet or outlet 7 has a nozzle-like shape to which a tube can be fitted. A blood cell suspension, such as blood, flows through the granulocyte collector while having contact with the granulocyte-separating material 1, whereby granulocytes are adsorbed or entrapped on the granulocyte-separating material 1 and thus separated from the other components of blood.

When the granulocyte collector according to the present invention is employed, granulocytes can be collected not only from blood collected from the body of the donor and having incorporated therein an anticoagulant, but also from blood continuously perfused according to the ectosomatic circulation method.

When the granulocyte collector of the present invention is used in the ectosomatic circulation method in large animals or human beings, commercially available artificial kidney circuits are connected upstream to and downstream from the granulocyte collector. The artificial kidney circuits and the collector are filled with a heparinized physiological saline solution before the start of the circulation operation. Blood is continuously taken out from a blood vessel in the surface portion of a body of an animal which has been loaded with heparin in an amount of 100 to 200 units per Kg of body weight, and perfusion is carried out for 2 hours by using a commercially available pump for an artificial kidney. The flow rate can be elevated to 300 ml/min, but when no shunt is used, the flow rate is ordinarily maintained below 50 ml/min. After completion of the perfusion, 500 ml of a heparinized physiological saline solution is passed through the collector to wash away non-adhering erythrocytes, lymphocytes and so on.

Then, by using a pulsating pump (for example, Model EP-B25 supplied by Kabushiki Kaisha Iwaki), 500 ml of a recovery liquid comprised of 300 ml of a physiological saline solution, 150 ml of serum or plasma and 50 ml of an anticoagulant (ACD-A solution comprising citric acid, sodium citrate and glucose) is passed through the collector to recover the granulocytes. It is preferred that the recovery liquid be caused to flow in a direction opposite to the flow direction of blood. Moreover, it is preferred that the pulsation rate be 40 to 120 pulses per minute and the difference between the maximum flow speed and the minimum flow speed be 0.3 to 10 cm per second. If the pulsation rate is lower than 40 pulses per minute, once separated from the separating material tend to be again adsorbed thereon, and if the pulsation rate exceeds 120 pulses per minute, the granulocytes are readily damaged. If the difference between the maximum flow speed and the minimum flow speed is smaller than 0.3 cm per second, re-adsorption of the granulocytes takes place. In contrast, if this speed difference is larger than 10 cm per second, the granulocytes are readily damaged. Recovery of granulocytes by utilizing a pulsating current is advantageous in that since tapping need not be performed, the recovery operation can be simplified and the amount of the recovery liquid can be minimized.

Instead of the above-mentioned method utilizing a pulsating current generated by a pulsating pump, there may be adopted a method in which a syringe or bag being connected to the collector and having an inner capacity of 20 to 500 ml is filled with a recovery liquid, and then, the recovery liquid is extruded out from the syringe or bag within several seconds to obtain a stream of the recovery liquid flowing at a flow speed of 1 to 300 cm per second, preferably 1 to 100 cm per second, whereby granulocytes are recovered. If the flow speed of a recovery liquid is lower than 1 cm per second, since there is no great difference between the flow speed of a recovery liquid and the flow speed of blood, the re-adsorption of granulocytes is readily caused. If the flow speed of the recovery liquid stream exceeds 300 cm per second, granulocytes are readily damaged. By the term "flow speed" used herein is meant an average value obtained by dividing the flow rate in volume (cm³/sec.) by the sectional area (cm²) of the path of a liquid within the vessel.

A phenomenon contrary to the above-mentioned phenomenon can be utilized. More specifically, there may be adopted a method in which a syringe or bag connected to the collector is suddenly expanded to cause the recovery liquid to flow into the interior of the syringe or bag through the interior of the collector.

In each of the foregoing two methods, it is preferred that the recovery liquid be caused to flow in the direction opposite to the direction of the flow of blood. Furthermore, granulocytes can be sufficiently collected also by reciprocating the recovery liquid in the collector by using a syringe or the like. Of course, granulocytes can be sufficiently recovered also by weak tapping.

The present invention will now be described in detail with reference to the following Examples that by no means limit the scope of the invention.

In the Examples, the granulocyte recovery percentage was calculated according to the following formula:

Recovery percentage (%) =

$$\frac{\text{number of granulocytes in recovery liquid}}{\text{number of total granulocytes before introduction of blood into separator}} \times 100$$

The granulocyte purity was expressed in terms of the percent of the number of granulocytes to the number of total leukocytes.

The granulocyte survival percentage was expressed in terms of the percent of the number of living granulocytes having a resistance to Trypan Blue dyeing to the total number of the granulocytes recovered in the recovery liquid.

The amount of the fatty acid derivative deposited on the fiber was determined by extracting the fatty acid derivative with an organic solvent, removing the organic solvent from the extract by evaporation and measuring the weight of the residue.

EXAMPLE 1

In 100 ml of diethyl ether was dissolved 1 g of oleic acid monoglyceric ester (having a melting point of 35.5° C.), and 5 g of 3 denier polyester fibers was dipped in the solution for 30 minutes. The excess of the solution was absorbed in a filter paper and thus removed. The fiber was dried at room temperature for 3 hours under reduced pressure to completely remove diethyl ether.

Figure 2:
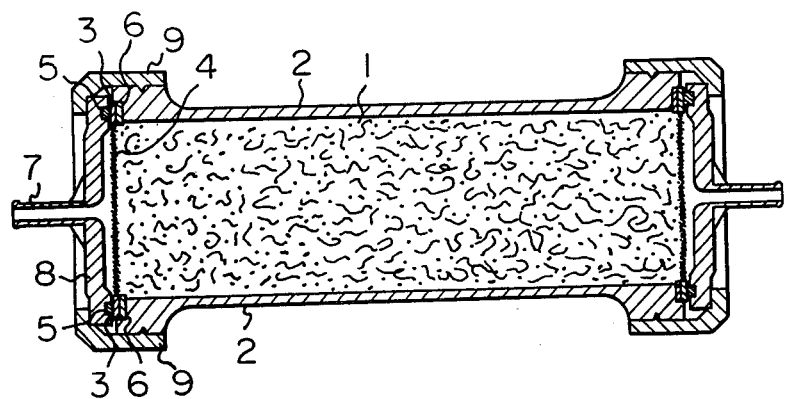

Then, 5 g of the so prepared granulocyte-separating material was uniformly packed in a column having a structure as shown in FIGS. 1 and 2, a diameter of 40 mm, a length of 40 mm and an inner capacity of 50 cm³. Silicone tubes were connected to the inlet and outlet of the vessel and the vessel was filled with a heparinized physiological saline solution.

Then, 1 l of fresh bovine blood in which heparin was incorporated in an amount of 1 unit per ml of blood and which was heated at 37° C. (the number of granulocytes was 4.2×10³/mm² and the granulocyte purity was 52%) was supplied into the column at a flow rate of 10 ml/min by a roller pump, and then, the interior of the granulocyte separator was washed with 100 ml of a heparinized physiological saline solution.

Then, 500 ml of the recovery liquid was caused to flow through the column at a pulsation rate of 60 pulses per minute by using a pulsating pump (electromagnetic metering pump Model EP-B25 supplied by Kabushiki Kaisha Iwaki) to recover the granulocytes. The recovery liquid was caused to flow in the direction opposite to the flow direction of the blood.

The recovery liquid comprised 300 ml of a physiological saline solution, 150 ml of plasma of the donor and 50 ml of an anticoagulant liquid (ACD-A solution).

The results are shown in Table I, below.

EXAMPLE 2

Stearic acid triglyceric ester having a melting point of 55° C. was deposited on a 2 denier nylon fiber in the same manner as described in Example 1, to prepare a granulocyte-separating material. Using this material, granulocytes were separated from bovine blood in the same manner as described in Example 1. The results are shown in Table I, below.

EXAMPLE 3

In 100 ml of chloroform was dissolved 200 mg of sphingomyelin, and 5 g of 3 denier nylon fibers was dipped in the sphingomyelin solution for 30 minutes, to prepare a granulocyte-separating material. Using this material, granulocytes were separated from bovine blood in the same manner as described in Example 1. The results are shown in Table I, below.

except that recovery of the granulocytes adsorbed on the separating material was carried out as follows. A syringe having an inner capacity of 100 cm$^3$ was filled with the recovery liquid, and then, 100 ml of the recovery liquid was extruded at a flow speed of 16 cm per second from the syringe and through the fiber-packed column. The results are shown in Table I, below.

COMPARATIVE EXAMPLE 1

The experiment was carried out under the same conditions as adopted in Example 1 except that an untreated 3 denier polyester fiber was used as the separating material instead of the oleic acid monoglyceric ester-supported polyester fiber. The results are shown in Table I, below.

COMPARATIVE EXAMPLE 2

The experiment was carried out under the same conditions as adopted in Example 1 except that ethyl lignocerate having a melting point of 54.8° C. was used as the fatty acid derivative. The results are shown in Table I, below.

TABLE I

| Example No. | Deposited Substance | | | Granulocyte recovery (%) | Purity of granulocytes (%) | Survival percentage of granulocytes (%) |
|---|---|---|---|---|---|---|
| | Kind | Amount (mg per gram of fiber) | Carrier | | | |
| 1 | Oleic acid monoglyceric ester | 30 | 3-denier polyester fiber | 37 | 97 | 95 |
| 2 | Stearic acid triglyceric ester | 35 | 2-denier nylon fiber | 34 | 95 | 93 |
| 3 | Sphingomyelin | 32 | 3-denier nylon fiber | 45 | 92 | 95 |
| 4 | Egg yolk lecithin | 28 | 3-denier polyester fiber | 53 | 96 | 96 |
| 5 | Egg yolk lecithin | 28 | 3-denier polyester fiber | 51 | 95 | 96 |
| Comparative Example 1 | Not added | — | 3-denier polyester fiber | 28 | 92 | 36 |
| Comparative Example 2 | Ethyl lignocerate | 25 | 3-denier polyester fiber | 29 | 86 | 78 |

EXAMPLE 4

Egg yolk lecithin was deposited on 3 denier polyester fibers in the same manner as described in Example 1, to prepare a granulocyte-separating material. Using this material, granulocytes were separated from bovine blood in the same manner as described in Example 1. The results are shown in Table I, below.

EXAMPLE 5

Granulocytes were separated from bovine blood under the same conditions as adopted in Example 4

We claim:

1. A granulocyte collector comprising a granulocyte-separating material packed in a vessel having a blood cell suspension introduction inlet and a blood cell suspension discharge outlet; said granulocyte-separating material comprising a carrier comprised of a fiber having a diameter of from 10 to 50 microns and packed in the vessel at a packing density of from 0.05 to 0.20 g/cm$^3$ and having supported thereon a fatty acid derivative containing a fatty acid moiety having 10 to 22 carbon atoms.

* * * * *